US00PP20964P2

(12) United States Plant Patent
Kolster

(10) Patent No.: US PP20,964 P2
(45) Date of Patent: Apr. 27, 2010

(54) ***DEUTZIA* PLANT NAMED 'KOLMASPRI'**
(50) Latin Name: *Deutzia×hybrida*
Varietal Denomination: Kolmaspri

(75) Inventor: Peter Rudolf Kolster, Boskoop (NL)

(73) Assignee: Kolster Beheer B.V., Boskoop (NL)

( * ) Notice: Subject to any disclaimer, the term of this patent is extended or adjusted under 35 U.S.C. 154(b) by 0 days.

(21) Appl. No.: 12/315,311

(22) Filed: Dec. 2, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Deutzia* plant named 'Kolmaspri', characterized by its upright plant habit; strong and erect flowering stems; freely flowering habit; white-colored flowers; and good garden performance.

2 Drawing Sheets

Botanical designation: *Deutzia×hybrida.*
Cultivar denomination: 'KOLMASPRI'.

BACKGROUND OF THE INVENTION

The present invention relates to a new and distinct cultivar of *Deutzia* plant, botanically known as *Deutzia×hybrida* and hereinafter referred to by the name 'Kolmaspri'.

The new *Deutzia* plant is a product of a planned breeding program conducted by the Inventor in Boskoop, The Netherlands. The objective of the breeding program is to create new *Deutzia* cultivars with strong and upright flowering stems and freely flowering habit.

The new *Deutzia* plant originated from a open-pollination in Boskoop, The Netherlands in 1999 of *Deutzia×hybrida* 'Mont Rose', not patented, as the female, or seed, parent with an unknown selection of *Deutzia×hybrida* as the male, or pollen, parent. The new *Deutzia* was discovered and selected by the Inventor as a single flowering plant from within the progeny of the stated open-pollination in a controlled environment in Boskoop, The Netherlands in 2004.

Asexual reproduction of the new *Deutzia* plant by cuttings in a controlled environment in Boskoop, The Netherlands since 2004, has shown that the unique features of this new *Deutzia* plant are stable and reproduced true to type in successive generations.

SUMMARY OF THE INVENTION

Plants of the new *Deutzia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kolmaspri'. These characteristics in combination distinguish 'Kolmaspri' as a new and distinct cultivar of *Deutzia:*

1. Upright plant habit.
2. Strong and erect flowering stems.
3. Freely flowering habit.
4. White-colored flowers.
5. Good garden performance.

Plants of the new *Deutzia* differ primarily from plants of the female parent, 'Mont Rose', in the following characteristics:

1. Plants of the new *Deutzia* have stronger and more erect flowering stems than plants of 'Mont Rose'.
2. Plants of the new *Deutzia* have shorter flowering stems than plants of 'Mont Rose'.
3. Plants of the new *Deutzia* are more freely flowering than plants of 'Mont Rose'.
4. Plants of the new *Deutzia* and 'Mont Rose' differ in flower color as plants of 'Mont Rose' have pink-colored flowers.

Plants of the new *Deutzia* can also be compared to plants of *Deutzia longifolia* 'Veitchii', not patented. In side-by-side comparisons conducted in Boskoop, The Netherlands, plants of the new *Deutzia* and 'Veitchii' differed primarily in the following characteristics:

1. Plants of the new *Deutzia* have stronger and more erect flowering stems than plants of 'Veitchii'.
2. Plants of the new *Deutzia* have smaller and lighter green-colored leaves than plants of 'Veitchii'.
3. Plants of the new *Deutzia* and 'Veitchii' differ in flower color as plants of 'Veitchii' have pink-colored flowers.

BRIEF DESCRIPTION OF THE PHOTOGRAPHS

The accompanying colored photographs illustrate the overall appearance of the new *Deutzia*, showing the colors as true as it is reasonably possible to obtain in colored reproductions of this type. Colors in the photographs may differ slightly from the color values cited in the detailed botanical description which accurately describe the colors of the new *Deutzia.*

The photograph on the first sheet comprises a side perspective view of a typical plant of 'Kolmaspri' grown in an outdoor nursery.

The photograph on the second sheet is a close-up view of typical inflorescences of 'Kolmaspri'.

DETAILED BOTANICAL DESCRIPTION

The aforementioned photographs and following observations, measurements and values describe plants grown in Boskoop, The Netherlands, under commercial practice during the spring in an outdoor nursery. During the production of the plants, day temperatures ranged from 14° C. to 25° C. and night temperatures ranged from 7° C. to 17° C. Plants had been growing for three years when the photographs and description were taken. In the following description, color references are made to The Royal Horticultural Society Colour Chart, 2007 Edition, except where general terms of ordinary dictionary significance are used.

Botanical classification: *Deutzia×hybrida* 'Kolmaspri'.

Parentage:

*Female, or seed, parent.*—*Deutzia×hybrida* 'Mont Rose', not patented.

*Male, or pollen, parent.*—Unknown selection of *Deutzia×hybrida*, not patented.

Propagation:

*Type.*—By cuttings.

*Time to initiate roots.*—About two weeks at 15° C. to 30° C.

*Time to produce a rooted young plant.*—About six months at 15° C. to 30° C.

*Root description.*—Fibrous, medium in thickness; creamy white in color.

*Rooting habit.*—Moderate branching; moderately dense.

Plant description:

*Plant form/habit.*—Upright plant habit; strong and erect flowering stems; moderately vigorous to vigorous growth habit.

*Branching habit.*—Freely branching habit with about 33 lateral branches developing per plant.

*Plant height.*—About 99.7 cm.

*Plant width* (*spread*).—About 117 cm.

*Primary lateral branches.*—Length: About 99 cm. Diameter: About 5 mm. Internode length: About 2.2 cm. Strength: Strong. Texture, developing: Densely pubescent. Texture, developed: Woody. Color, developing: Close to 137C to 137D. Color, developed: Between 199D to 200D.

Foliage description:

*Arrangement.*—Opposite, simple.

*Length, largest leaves.*—About 10.3 cm.

*Width, largest leaves.*—About 3.7 cm.

*Shape.*—Narrowly ovate.

*Apex.*—Acute.

*Base.*—Obtuse.

*Margin.*—Serrate.

*Texture, upper and lower surfaces.*—Pubescent; rugose.

*Venation pattern.*—Pinnate.

*Color.*—Developing leaves, upper surface: Close to 137B. Developing leaves, lower surface: Close to 191A to 191B. Fully expanded leaves, upper surface: Close to 137A to 137B; venation, close to 144B to 144C. Fully expanded leaves, lower surface: Close to 138A to 138B; venation, close to 148A.

*Petioles.*—Length: About 7 mm. Diameter: About 3 mm. Texture, upper and lower surfaces: Pubescent. Color, upper and lower surfaces: Close to 144A to 144B.

Flower description:

*Flower type/habit.*—Single rotate flowers arranged in terminal thyrsus; flowers face mostly outwardly. Thyrsus roughly conical in shape. Freely flowering habit with about 40 flowers per inflorescence.

*Fragrance.*—Faintly fragrant; sweet and pleasant.

*Natural flowering season.*—Continuously flowering during the late spring in The Netherlands.

*Postproduction longevity.*—Flowers last about six days on the plant; flowers last about six days as a cut flower; flowers not persistent.

*Flower buds.*—Height: About 8 mm. Diameter: About 5.5 mm. Shape: Oblong. Color: Close to 155C.

*Inflorescence height: About* 8.6 cm.

*Inflorescence diameter: About* 5.2 cm.

*Flower diameter: About* 2.3 cm.

*Flower depth: About* 1.6 cm.

*Petals.*—Quantity per flower: Typically five in a single whorl. Length: About 1.3 cm. Width: About 6 mm. Shape: Elliptic. Apex: Broadly acute. Margin: Entire. Texture, upper and lower surfaces: Smooth, glabrous. Color: Developing petals, upper and lower surfaces: Close to 155C. Fully expanded petals, upper and lower surfaces: Close to NN155D.

*Sepals.*—Quantity per flower: Typically five in a single whorl, fused towards the base; calyx campanulate. Length: About 2.5 mm. Width: About 1.5 mm. Shape: Ovate. Apex: Acute. Margin: Entire. Texture, upper and lower surfaces: Smooth, glabrous. Color: Developing and fully expanded sepals, upper surface: Close to 144B. Developing and fully expanded sepals, lower surface: Close to 138B.

*Peduncles.*—Length: About 7.2 cm. Diameter: About 1 mm. Strength: Moderately strong. Texture: Smooth, glabrous. Color: Close to 152A.

*Pedicels.*—Length: About 4 mm. Diameter: About 0.75 mm. Strength: Moderately strong. Texture: Smooth, glabrous. Color: Close to 152A.

*Reproductive organs.*—Stamens: Quantity per flower: Typically ten. Filament length: About 9 mm. Filament color: Close to NN155D. Anther shape: Circular, flattened. Anther length: About 1 mm. Anther color: Close to 11A. Pollen amount: Abundant. Pollen color: Close to 14B. Pistils: Quantity per flower: Three. Pistil length: About 1.3 cm. Stigma shape: Club-shaped, narrow. Stigma color: Close to N144A. Style length: About 1.2 cm. Style color: Close to 145C to 145D. Ovary color: Close to N138C.

*Seed/fruit.*—Seed and fruit development have not been observed.

Disease/pest resistance: Plants of the new *Deutzia* have not been observed to be resistant to pathogens or pests common to *Deutzia*.

Garden performance: Plants of the new *Deutzia* have been observed to have good garden performance and tolerate rain, wind and temperatures ranging from about −20° C. to about 40° C.

It is claimed:

1. A new and distinct *Deutzia* plant named 'Kolmaspri' as illustrated and described.

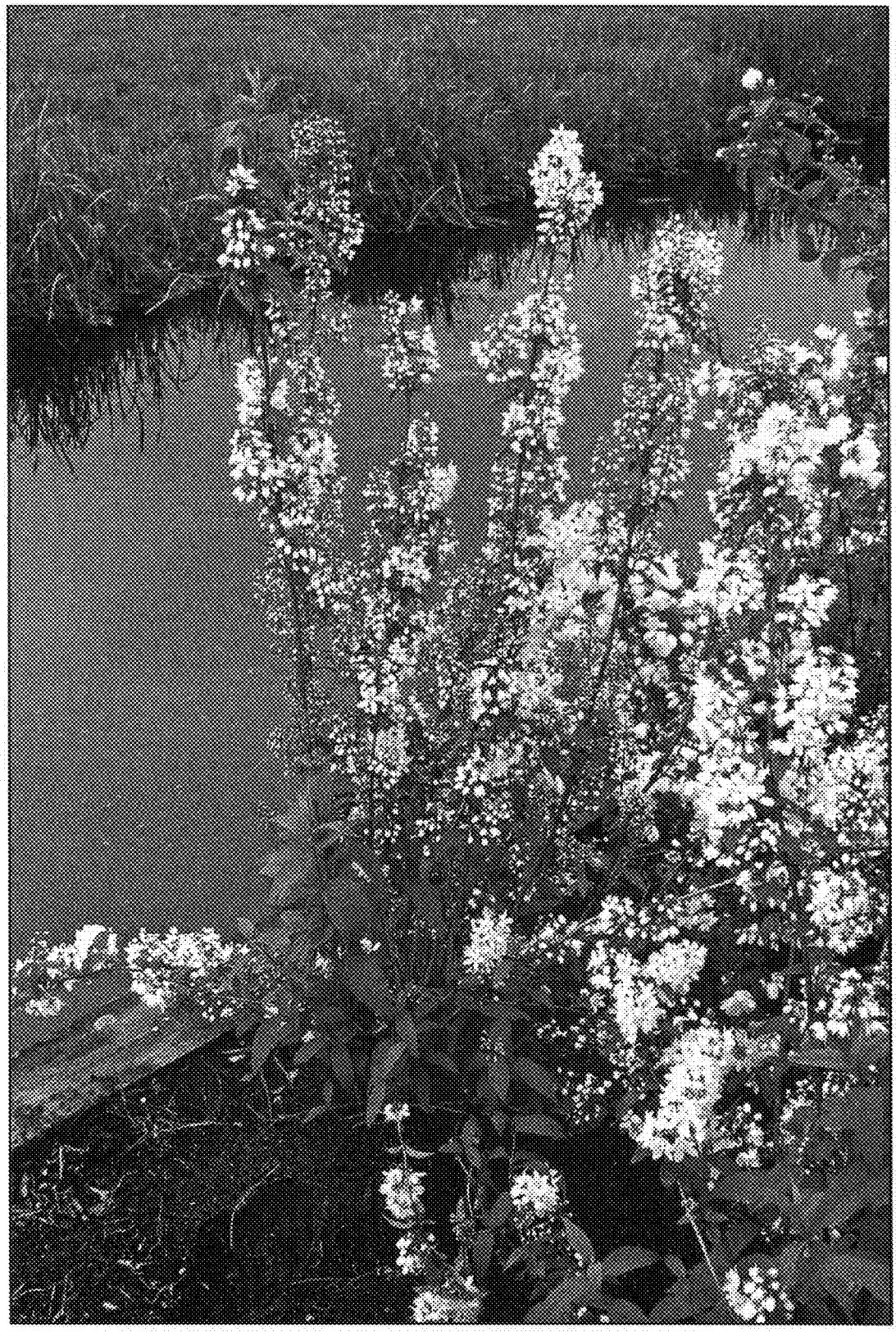

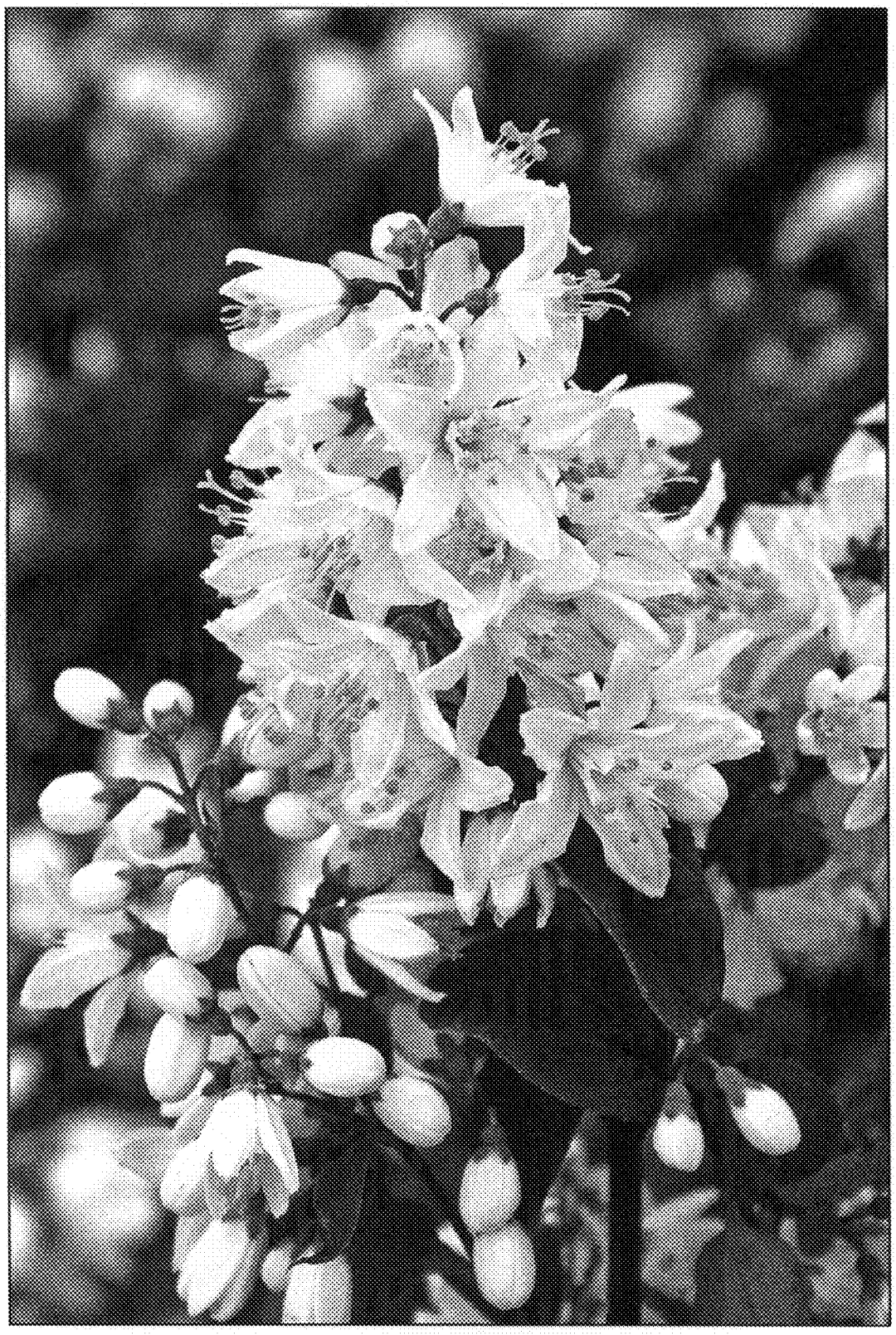

* * * * *